United States Patent
Humbert et al.

(10) Patent No.: US 8,707,781 B2
(45) Date of Patent: Apr. 29, 2014

(54) SENSOR HAS COMBINED IN-PLANE AND PARALLEL-PLANE CONFIGURATION

(75) Inventors: Aurelie Humbert, Brussels (BE); Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 328 days.

(21) Appl. No.: 13/063,325

(22) PCT Filed: Sep. 10, 2009

(86) PCT No.: PCT/IB2009/053959
§ 371 (c)(1),
(2), (4) Date: Mar. 10, 2011

(87) PCT Pub. No.: WO2010/029507
PCT Pub. Date: Mar. 18, 2010

(65) Prior Publication Data
US 2011/0185810 A1 Aug. 4, 2011

(30) Foreign Application Priority Data
Sep. 11, 2008 (EP) .................................... 08105307

(51) Int. Cl.
*G01N 27/22* (2006.01)
(52) U.S. Cl.
USPC ........... 73/335.04; 73/31.05; 73/73; 361/286; 361/303; 324/689
(58) Field of Classification Search
USPC .......... 73/335.03–335.05; 324/663, 664, 689; 361/278, 286, 303, 306.03, 311–313
See application file for complete search history.

(56) References Cited

U.S. PATENT DOCUMENTS

| 4,429,343 | A | | 1/1984 | Freud |
| 4,920,451 | A | * | 4/1990 | Sakai et al. .................... 361/286 |
| 5,069,069 | A | * | 12/1991 | Miyagishi et al. .......... 73/335.04 |
| 6,222,376 | B1 | * | 4/2001 | Tenney, III ..................... 324/664 |

(Continued)

FOREIGN PATENT DOCUMENTS

| DE | 44 33 102 A1 | 3/1996 |
| DE | 197 10 358 A1 | 9/1998 |

(Continued)

OTHER PUBLICATIONS

"Choosing a Humidity Sensor", Denes K. Roveti, http://www.sensorsmag.com/sensors/humidity-moisture/choosing-a-humidity-sensor-a-review-three-technologies-840, Jul. 1, 2001.*

(Continued)

*Primary Examiner* — Hezron E Williams
*Assistant Examiner* — Alexander Mercado

(57) ABSTRACT

A sensor senses a magnitude of a physical parameter of the sensor's environment. The sensor has first and second electrodes, and a material layer between them. The material has an electrical property, e.g., capacitance or resistance, whose value depends on the magnitude of the physical parameter. The first electrode is formed in a first layer, and the second electrode is formed in a second layer, different from the first layer. The first layer has a trench and an elevation next to the trench. The trench has a bottom wall and a side wall. The material is positioned on the bottom wall and on the side wall and on top of the elevation. The trench accommodates at least a part of the second electrode. The second electrode leaves exposed the material formed on top of the elevation.

11 Claims, 5 Drawing Sheets

(56) References Cited

U.S. PATENT DOCUMENTS

| | | | |
|---|---|---|---|
| 6,690,569 | B1 | 2/2004 | Mayer et al. |
| 6,742,387 | B2 * | 6/2004 | Hamamoto et al. ........ 73/335.04 |
| 7,159,471 | B2 * | 1/2007 | Fortune et al. ................... 73/780 |
| 7,222,531 | B2 * | 5/2007 | Isogai et al. ............... 73/335.04 |
| 7,742,277 | B2 * | 6/2010 | Shinoda et al. ............... 361/311 |
| 2002/0109959 | A1 * | 8/2002 | Toyoda et al. ................ 361/311 |
| 2005/0008061 | A1 | 1/2005 | Kaneko |
| 2005/0028588 | A1 * | 2/2005 | Mitter ......................... 73/335.04 |
| 2006/0174693 | A1 * | 8/2006 | Chen et al. .................... 73/29.01 |
| 2009/0237858 | A1 * | 9/2009 | Steeneken et al. ............ 361/278 |

FOREIGN PATENT DOCUMENTS

| | | | |
|---|---|---|---|
| DE | 101 52 608 | C2 | 5/2003 |
| DE | 10152608 | * | 5/2003 |
| EP | 0 395 349 | A2 | 10/2009 |
| JP | 2004-037405 | | 2/2004 |
| JP | 2004-037405 | A | 2/2004 |

OTHER PUBLICATIONS

English Translation of DE 10152608.*

Seiyama, Testro; "Chemical Sensor Technology, vol. 1—Chemical Sensors—Current State and Future Outlook"; Elsevier, Tokyo, JP; 15 pages (1988).

Niwa, Osamu, et al; "Fabrication and Characteristics of Vertically Separated Interdigitated Array Electrodes"; J. Electroanalytical Chemistry & Interfacialelectro Chemistry, vol. 267, No. 1-2; Elsevier, Amsterdam, NL,; pp. 291-297 (Aug. 10, 1989).

Krutovertsev, S. A, et al., "Integrated Multifuncational Humidity Sensor"; Sensors and Actuators, A 62; pp. 582-585; (1997).

Qu, Wenmin, et al.; "A Novel Thick-Film Ceramic Humidity Sensor"; Sensors and Actuators B, vol. 40, No. 2-3; Elsevier Sequoia S.A., Lausanne, CH; pp. 175-182 (May 15, 1997).

Docmeki, Mehmet, et al.; "A High-Sensivity Polimide Capacitive Relative Humidity Sensor for Monitoring Anodically Bonded Hermetic Micropackages"; Journal of Microelectromechanical Systems, vol. 10, No. 2; pp. 197-203 (Jun. 2001).

Yang, Ya Ling, et al; "Improvement of Polyimide Capacitive Humidity Sensor by Reactive Ion Etching and Novel Electrode Design"; IEEE Proceedings Sensors 2002, vol. 1; pp. 511-514 (2002).

Yonggui, D. "Sensing Technique and System", Tsinghua University Press Publisher, Beijing China, pp. 206-208 (Jun. 2006).

Laconte, J., et al; "High-Sensivity Capacitive Humidity Sensor Using 3-Layer Patterned Polyimide Sensing Film"; Proceedings of IEEE, Sensors, vol. 1; pp. 372-377 (2003).

Sen, Ashis Kumar, et al; "Modeling and Optimization of a Microscale Capacitive Humidity Sensor for HVAC Application"; IEEE Sensors Journal vol. 8, No. 4; pp. 333-340 (Apr. 2008).

International Search Report for Application PCT/IB2009/053959 (Dec. 8, 2009).

* cited by examiner

SENSOR HAS COMBINED IN-PLANE AND PARALLEL-PLANE CONFIGURATION

FIELD OF THE INVENTION

The invention relates to a device, e.g., an electronic circuit, comprising a sensor, e.g., a capacitive sensor or a resistive sensor, for sensing a magnitude of a physical parameter of an environment of the sensor, e.g., humidity. The sensor comprises a first electrode formed in a first layer, a second electrode formed in a second layer and a material between the first and second electrodes. The material has an electrical property, whose value depends on the magnitude of the physical parameter.

BACKGROUND ART

Such sensors are well known in the art. As an example of such a sensor, a capacitive humidity sensor is considered in the next paragraphs.

Humidity sensing is of great importance in many industrial applications, including monitoring of pharmaceutical products, biomedical products, food items, beverage storage and logistics (by use of e.g., RFID-based sensor logging equipment), the automotive industry, semiconductors industry, etc. The acronym "RFID" stands for radio-frequency identification. For the food monitoring application for example, measuring the relative humidity inside the food package is necessary to monitor the quality of the product, as excessive moisture content will lead to premature spoilage. In such application, the miniaturization of the humidity sensors is also a key element. For these reasons, integrating the humidity micro-sensors using integrated circuitry (IC) technology, e.g., CMOS IC technology, decreases the cost of the processing, and gives an advantageous integrated solution.

The majority of the humidity sensors, commercially available nowadays, have a capacitive sensor configuration. The capacitor's electrodes are electrically isolated from one another by means of a suitable dielectric material. The material's dielectric constant has a value, which depends on the magnitude of the relative humidity. As a result, the capacitance depends on the relative humidity. Therefore, if the capacitance determines the functional behavior of an electronic circuit (e.g., RC-time, oscillating frequency, etc.), the monitoring of this behavior enables to determine the relative humidity.

The capacitor in a capacitive sensor can have one of several spatial configurations, taking into account the fact that the dielectric material should be exposed to the ambient air in operational use of the sensor.

A first configuration is referred to as the parallel-plate capacitor (or parallel plane capacitor) configuration. Herein, a dielectric layer, made from a thin polymer film or a metal oxide, is sandwiched between two metal electrodes. The upper electrode can be patterned or made porous, typically using gold (Au) so that water vapor in the air can reach the dielectric layer. The patterned electrode is configured to protect the dielectric layer from contamination and exposure to condensation. For examples of such a sensor, see, e.g., EP 0 395 349; "Integrated multifunctional humidity sensor", S. A. Krutovertsev et al., Sensors and Actuators, A 62 (1997), pp. 582-585; "Modeling and Optimization of a Microscale Capacitive Humidity Sensor for HVAC Applications", A. K. Sen et al., IEEE Sensors Journal. Vol. 8 (4), April 2008, pp. 333-340; EP 0 395 949; and "Improvement of polyimide capacitive humidity sensor by reactive ion etching and novel electrode design", Y. L. Yang et al., IEEE Proceedings Sensors 2002, Vol. 1, pp. 511-514

Improvements to such sensor relate to, e.g., the design of the upper electrode, the adding of a heating element to control sensor sensitivity, the patterning also of the bottom electrode. As to the latter feature, openings are made in the dielectric material using the top metal grid of the upper electrode as a hard-mask. Thus, the area of the dielectric material exposed to the ambient air is increased. The bottom electrode is patterned as well, but is completely covered by the dielectric material. For more details see, e.g., "A high-sensitivity polyimide capacitive relative humidity sensor for monitoring anodically bonded hermetic micropackages", M. Docmeki et al., Journal of Microelectromechanical Systems, (2001) Vol. 10 pp. 197-203.

A second configuration is referred to as an in-plane capacitor. In such a capacitor, the two electrodes are formed in the same layer on top of a substrate, and the tops of the electrodes are coated by the dielectric material. The electrodes may be shaped as a pair of interlocking combs. This electrode pattern is also referred to as interdigitated electrodes (IDE). Examples of capacitive humidity sensors using the in-plane configuration are disclosed in, e.g., U.S. Pat. No. 7,222,531; U.S. Pat. No. 6,742,387; U.S. Pat. No. 6,690,569; U.S. Pat. No. 6,222,376; U.S. Pat. No. 4,429,343; US 2002/0109959; and JP 2004-037405. The publication "High-Sensitivity Capacitive Humidity Sensor Using 3-Layer Patterned Polyimide Sensing Film", J. Laconte et al., Proceedings of IEEE, Sensors, October, 2003, Vol. 1, pp 373-377, discloses an improved version of the IDE configuration. The capacitive humidity sensor considered in this publication is based on an IDE configuration and a polyimide sensitive layer. Aluminum interdigitated electrodes are formed with fingers of 1 μm width, and the distance between two adjacent fingers is 1 μm. The electrodes are deposited on a first insulating polyimide layer and are covered by two more polyimide layers. The upper polyimide layer features a regular array of holes to increase the active surface area.

SUMMARY OF THE INVENTION

The inventors have realized that the sensor structure can be improved with regard to its sensitivity, by means of combining features of the parallel-plane configuration with features of the in-plane configuration. Above discussion relates to known humidity sensors, in a capacitive implementation. However, the invention relates to the spatial configuration of the combination of the electrodes and the material sandwiched in between, and is therefore also applicable to capacitive or resistive sensors with a material sensitive to environmental parameters other than humidity.

More specifically, the inventors propose a device comprising a sensor for sensing a magnitude of a physical parameter of an environment of the sensor. The sensor comprises a first electrode, a second electrode and a material between the first and second electrodes. The material has an electrical property, whose value depends on the magnitude of the physical parameter. The first electrode is formed in a first layer, and the second electrode is formed in a second layer. The first layer has a trench and an elevation next to the trench. The trench has a bottom wall and a side wall. The material is positioned on the bottom wall and on the side wall and on top of the elevation. The trench accommodates at least a part of the second electrode. The second electrode leaves exposed the material formed on top of the elevation. In this configuration, both electrodes are patterned and embedded, with the layer of sensitive material in between. Both bottom wall and side wall of the trench contribute to the effective electrical behavior of the sensor.

In an embodiment, the material is formed in multiple spatially separated bands across the trench and the elevation. As a result, the sidewalls of neighboring bands of the material layer, i.e., the side walls of adjacent bands facing each other, increase the contact area with the environment, and thus the sensor's sensitivity to the physical parameter.

In a further embodiment, the material on top of the elevation has one or more grooves or holes. The holes or grooves only occur in the material layer where exposed by the second electrode, and not in the material's portions sandwiched between the first and second electrodes. The grooves or holes pattern the material on top of the elevations so as to further increase the contact area with the environment.

In a further embodiment, the sensor is configured as a capacitive sensor, and the material serves as a dielectric, whose dielectric constant depends on a magnitude of the physical parameter. For example, the physical parameter is humidity, and the material comprises a humidity sensitive substance such as, at least one of: polyimide, silicon carbide, a metal oxide, and silicon nitride. Capacitors are formed in the horizontal direction at locations, where the dielectric material covers the side wall of the trench, as well as in the vertical direction at locations where the dielectric material covers the bottom wall of the trench. The invention thus combines an in-plane design and a parallel-plane design and is relatively simple to manufacture in a photolithographic process.

In a further embodiment, the device comprises a transponder, e.g., an RFID tag, accommodating the sensor.

BRIEF DESCRIPTION OF THE DRAWING

The invention is explained in further detail, by way of example and with reference to the accompanying drawing, wherein.

Throughout the Figures, similar or corresponding features are indicated by same reference numerals.

DETAILED EMBODIMENTS

Figure 1:
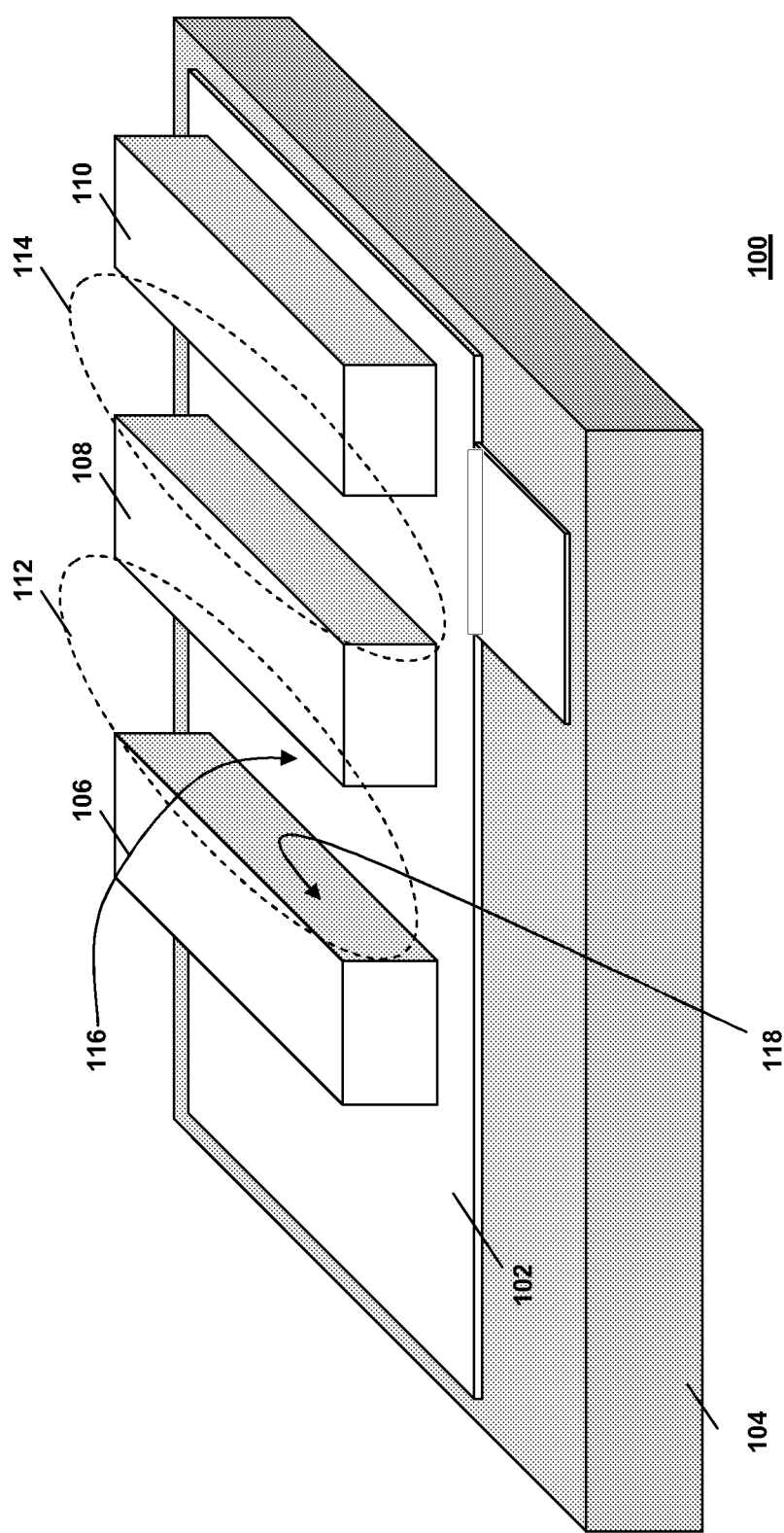
FIGS. 1, 2 and 3 are diagrams illustrating different phases in the fabrication of an embodiment of a sensor in the invention.
Figure 2:
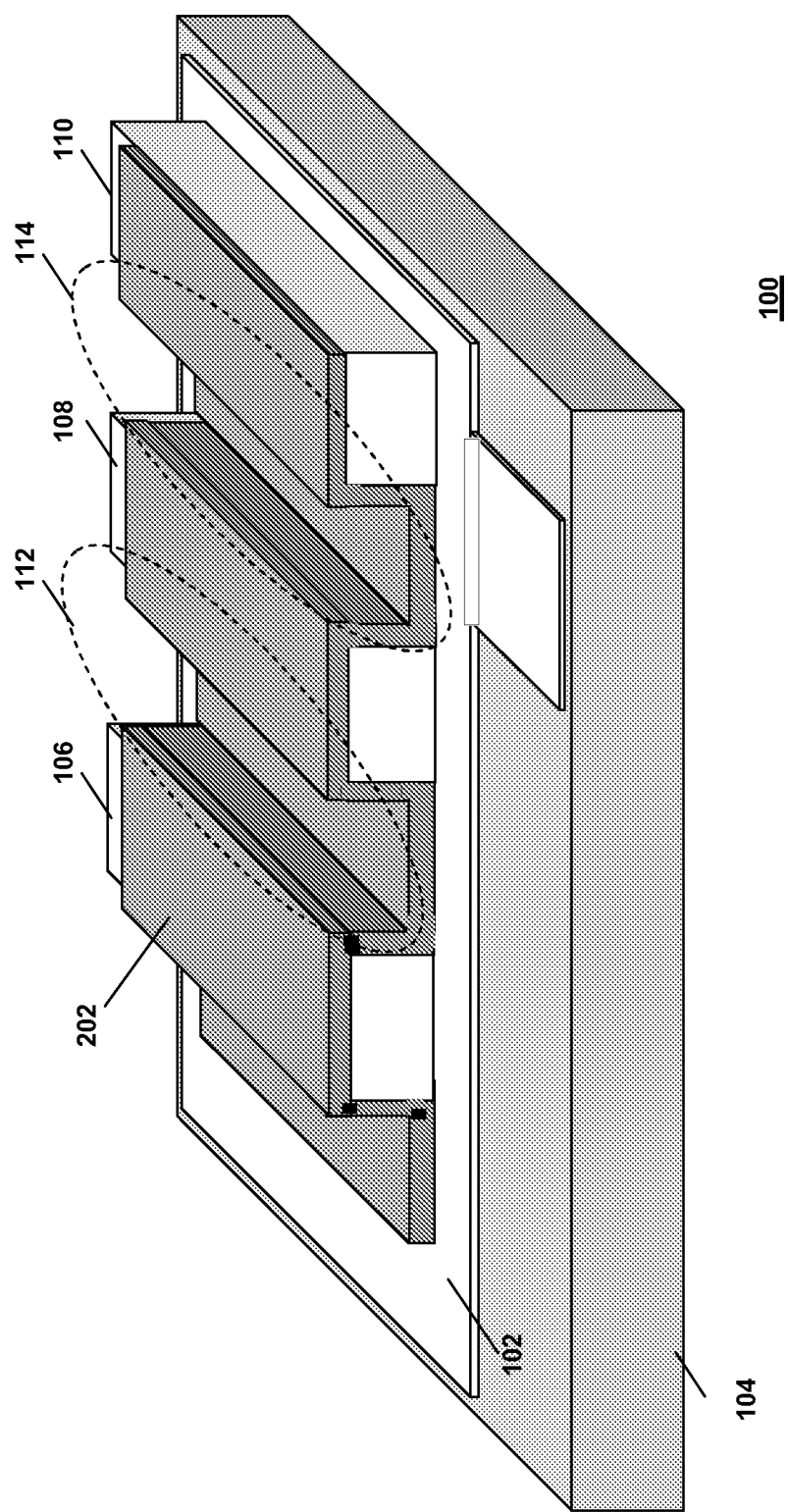
Figure 3:
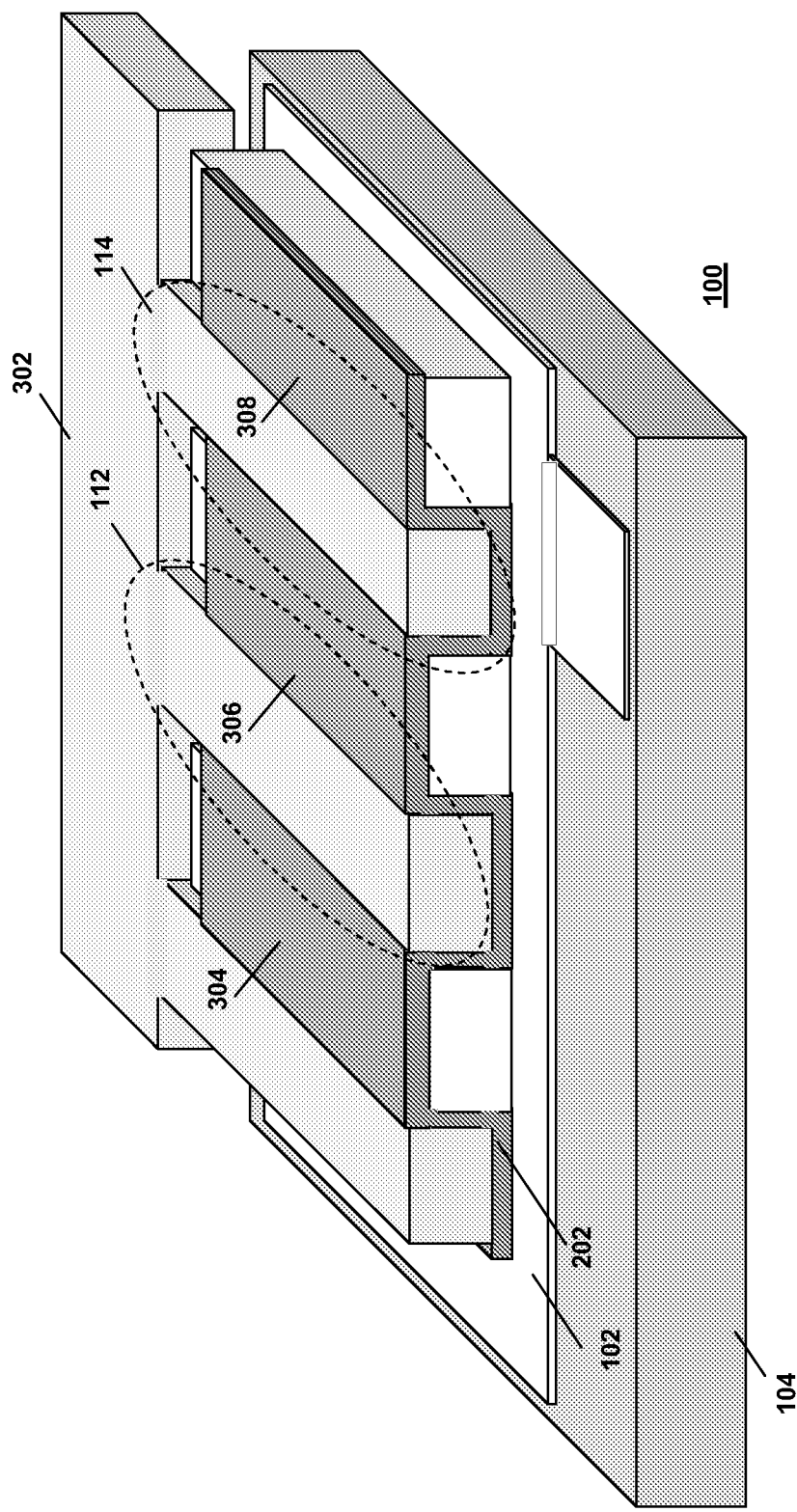

FIGS. 1-3 are diagrams illustrating in perspective the fabrication of an embodiment of a capacitive sensor 100 in the invention. Sensor 100 is preferably fabricated in a photolithographic technology, e.g., as used in the manufacturing of integrated circuitry (IC) or a printed circuit board (PCB).

FIG. 1 illustrates a result of a fabrication step wherein an electrically conductive layer 102 is fabricated on an isolating substrate 104. Layer 102 is going to serve as an electrode of capacitive sensor 100. Layer 102 is patterned so as to have elevations 106, 108, . . . , 110 that define trenches 112, . . . , 114. Each of trenches 112-114 has a bottom wall and two side walls. In order to not obscure the drawing, a bottom wall 116 and a side wall 118 have been indicated for trench 112 only.

FIG. 2 illustrates a result of a fabrication step wherein a layer 202 of a dielectric material is formed conformal to the pattern of elevations 106-110 and trenches 112-114. Note that the bottom walls and side walls of trenches 112-114 have been covered by layer 202. The dielectric material of layer 202 has a dielectric constant whose value depends on the magnitude of the physical parameter. Examples of the physical parameter and associated materials for layer 202 are discussed in further detail below.

FIG. 3 illustrates a result of a fabrication step wherein an electrically conductive layer 302 is fabricated to fill trenches 112 and 114. Layer 302 is going to serve the other electrode of sensor 100. Layer 302 leaves top portions 304, 306 and 308 of layer 202 exposed to an environment of sensor 100 so as to have the value of the dielectric constant be affected by a physical parameter characteristic of the environment.

Mainly the parts of layer 202 that are sandwiched between layers 102 and 302 determine the capacitance of sensor 100, and therefore also its sensitivity. The larger part of top portions 304-306 is not sandwiched between electrodes 102 and 302. As a result, the contribution of top portions 304-308 to the overall capacitance is of a lower order effect and is determined merely by fringe electric fields.

Assume now, by way of example, that layer 202 is made of a dielectric material, which is sensitive to humidity in the ambient air. Sensor 100 is then implemented as a humidity sensor. Sensor 100 is exposed to humidity at the upper surface portions 304-308 of layer 202. The humidity captured at portions 304-308 needs to diffuse to the parts of layer 202 sandwiched between layers 102 and 302.

Figure 4:
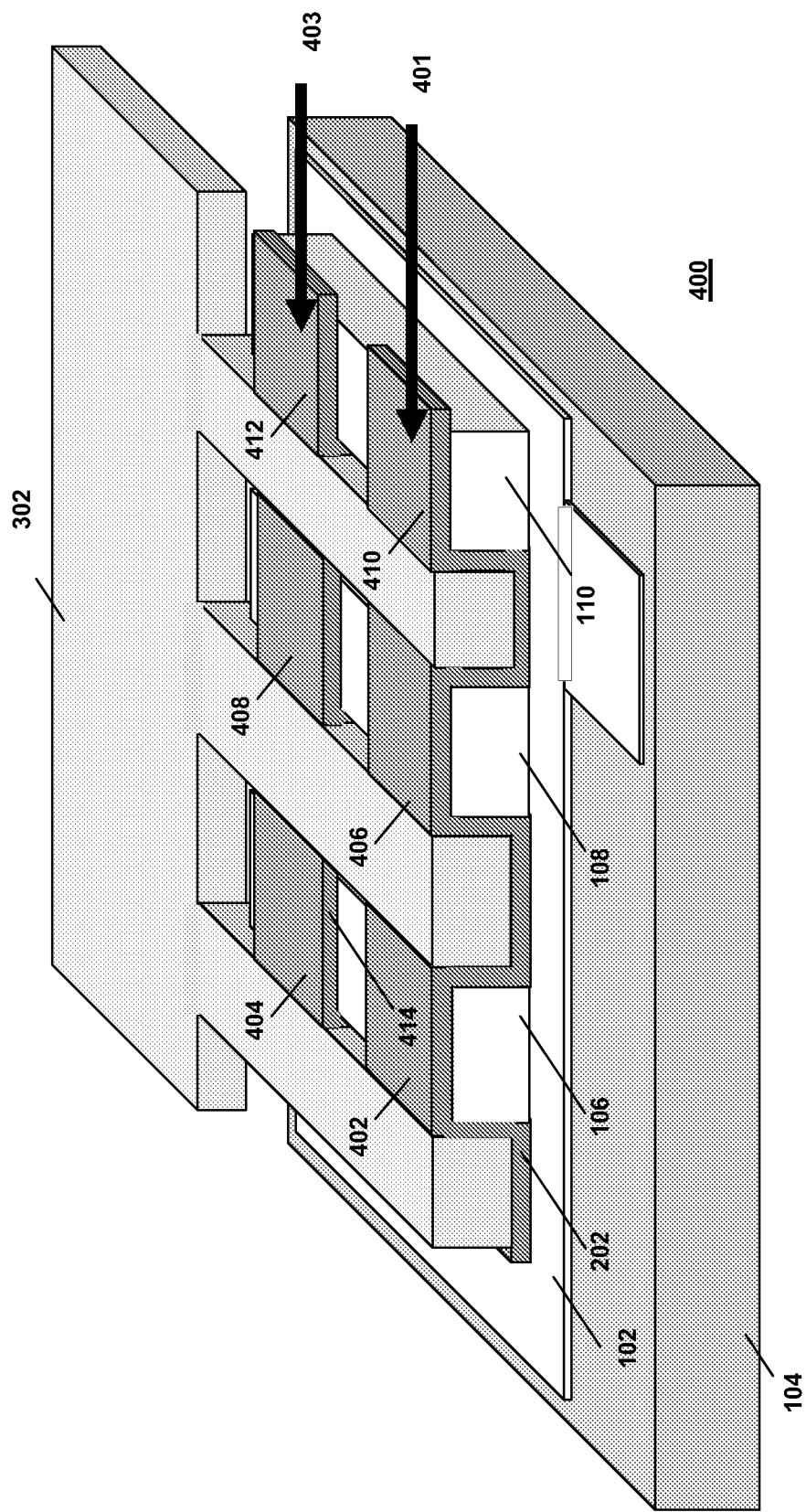
FIG. 4 is a diagram illustrating a phase in the fabrication of another embodiment of a sensor in the invention.

FIG. 4 illustrates a result of a similar fabrication process as discussed with reference to FIGS. 1-3. Sensor 400 made in this process differs from sensor 100 in that layer 202 is composed of multiple bands 401, . . . , 403 running in parallel across elevations 106-110 and trenches 112-114 between elevations 106-110. Trenches 112-114 have not been indicated in FIG. 4 in order to not obscure the drawing, but they are formed as discussed under FIG. 1. In sensor 400, top portions 402, 404, 406, 408, 410, . . . , 412 of dielectric layer 202 are exposed to the environment.

An advantage of the configuration of sensor 400 over that of sensor 100 is that the openings between neighboring bands facilitate penetration of the agent (humidity in above example) in the ambient air or ambient fluid into the relevant portions of layer 202 that contribute to the capacitance, namely to those portions sandwiched between electrodes 102 and 302. Per unit area of such sandwiched portion, there is a larger contact area with the ambient air or fluid than in sensor 100. The contact area includes the side surfaces of bands 401 and 403, i.e., those surfaces on band 401 that face similar side surfaces on band 403. For clarity only a single one of such side surfaces, here surface 414, has been indicated in order to not obscure the drawing. Note that the thickness of layer 202 need not be uniform throughout the sensor. For example, top portions 402 are thicker than the sandwiched portions using an extra process step. As a result, the area of the side surfaces is increased, and therefore the capturing area per unit area of the sandwiched portion of layer 202, thus increasing sensitivity of the sensor.

Figure 5:
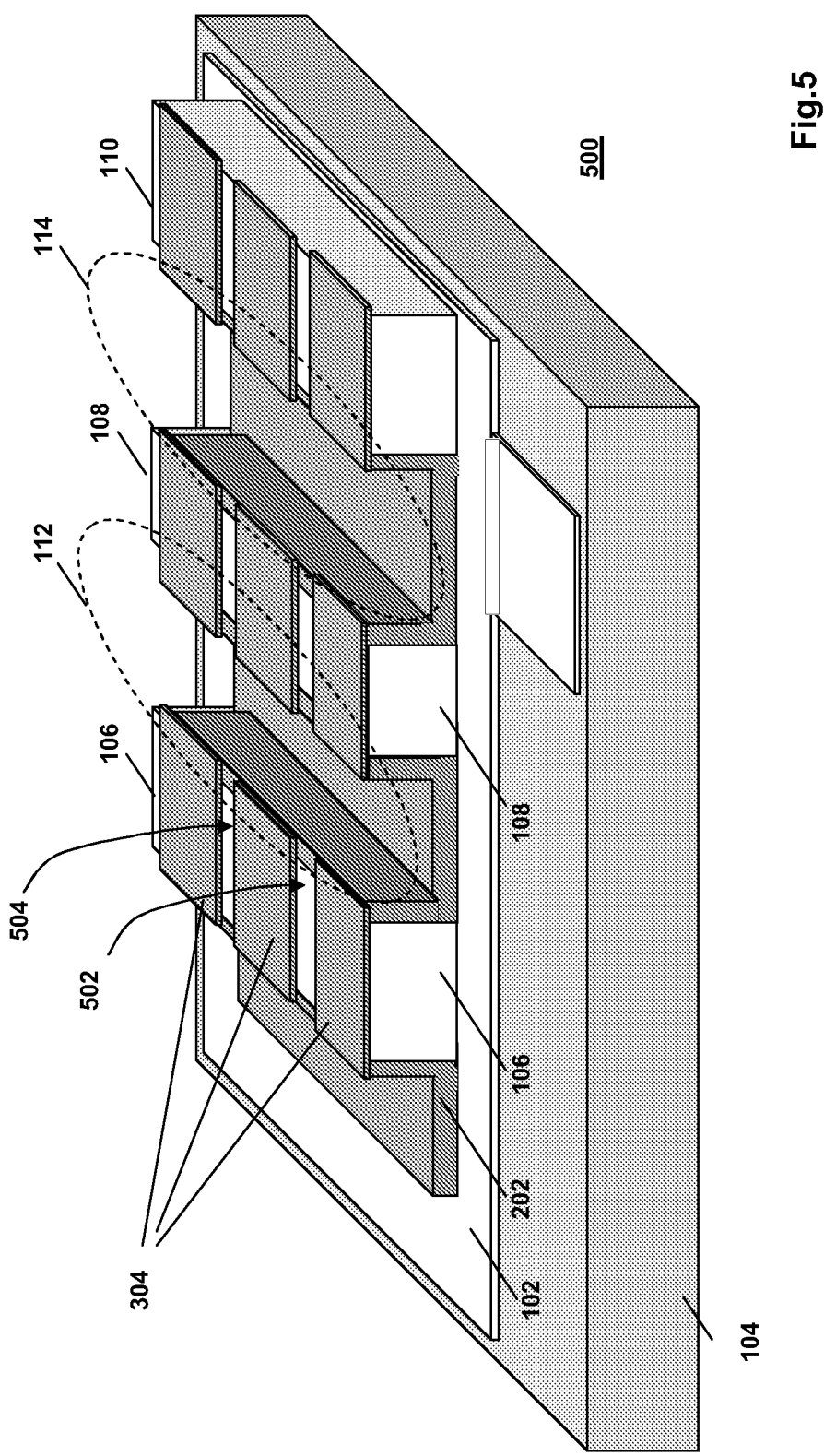
FIG. 5 is a diagram illustrating a phase in the fabrication of a further embodiment of a sensor in the invention.

FIG. 5 is a diagram illustrating in perspective a part of a further embodiment 500 of a sensor in the invention. In order to not obscure the drawing, second electrode 302 is not indicated. A further increase of the sensitivity is brought about by grooves or holes (not shown) in top portions 304-308 of sensor 100 or in top portions 402-412 of sensor 400, but not in the portions of layer 202 that are sandwiched between electrodes 102 and 302. FIG. 5 illustrates the grooves for a configuration of sensor 100. FIG. 5 only indicates two of these grooves, groove 502 and groove 504, and does not show electrode 302 in order to not obscure the drawing. Grooves 502-504 are preferably made after electrode 302 is provided occupying trenches 112 and 114. The grooves or holes in top portions 304-308 or 402-412 further increase the contact area across which layer 202 is exposed to the environment. Note that such grooves or holes do not affect the area of the sandwiched portions that eventually determine the capacitance. The grooves 502-504 run in a direction substantially perpendicular to the main direction of trenches 112-114, but another direction may be chosen.

The drawings do not indicate other layers provided in the process, e.g., isolation layers between electrode layers 102 and 302, or protection layers to cover elevations 106-110 between top portions 402-412. The fabrication and positioning of such additional layers are clear to the person skilled in the art of, e.g., semiconductor manufacturing, and such layers are not discussed herein in further detail.

Electrode layers 102 and 302 can be made from similar materials or from different materials. For example, electrode 102 is made of aluminum (Al), and electrode 302 is made from copper (Cu). Dielectric layer 202 is made of a material whose dielectric properties depend on the environmental parameter to be measured and that is suitable for being used in the photolithographic process. For example, is sensors 100 and 400 are to be used as a humidity sensor, the sensitive material can be one of: polyimide, silicon carbide, metal oxide, silicon nitride.

In an embodiment of the invention, sensitive material layer 202 can be applied as a conformal deposition, using, e.g., a spin-on process, physical vapor deposition (PVD), chemical vapor deposition (CVD), etc. In a conformal deposition, all exposed surfaces are covered regardless of their orientation. For example, also the areas of elevations 106-110 are covered that face the bar of electrode 302 that connects the parts of electrode 302 accommodated in trenches 112-114.

Above examples discuss a capacitive sensor, whose operation is based on detecting a change in capacitance as a result of a change in the physical parameter representative of the environment of the sensor. However, the same topographical configuration can be used for a resistive sensor. In a resistive sensor, a change in electrical resistance is detected as a result of a change in the physical parameter representative of the environment of the sensor.

Below is a table with examples of sensitive materials suitable for use in layer 202 of a capacitive or resistive sensor for sensing a particular physical parameter, and patterned with a lithographic process and, where applicable, a subsequent etch.

| Gas | Capacitive type | Resistive type |
| --- | --- | --- |
| Humidity | $Al_2O_3$, polyimide, $TiO_2$, $SiO_2$, SiC, polyesters, PMMA (Polymethyl methacrylate), BCB (Benzocyclobutene), polysulfates, cellulose acetate butyrate, porous silicon, . . . | $Al_2O_3$, $TiO_2$, spinels ( $BaTiO_3$, $ZnCr_2O_4$, $K_2CrO_4$, $MgAl_2O_4$), . . . |
| $H_2$ | Ferroelectric materials | Palladium-based materials |
| $CO_2$ | Fluoropolymer, CuO mixed with $BaSnO_3$, $SrTiO_3$, $CaTiO_3$, ZnO or $BaTiO_3$ | $In_2Te_3$, |
| $O_2$ | Zirconium oxide, Irridium oxides, . . . | |
| Ethylene | $SnO_2$ based film, . . . | |
| $NH_3$ | Porous SiC, $TiO_2$ | $SnO_2$, $WO_3$, metal oxides, polypyrrole, polyaniline |

For further examples of sensitive materials suitable for use in layer 202 see, e.g., Table 2 "Materials Used as Chemical Sensor Elements" in "Chemical Sensor Technology", Vol. 1, Ed. Tetsuro Seiyama, Elsevier 1988.

The invention claimed is:

1. A device comprising a sensor for sensing a magnitude of a physical parameter of an environment of the sensor, wherein:
   the sensor comprises a first electrode, a second electrode and a material between the first and second electrodes;
   the material has an electrical property, whose value depends on the magnitude of the physical parameter;
   the first electrode is formed in a first layer, and the second electrode is formed in a second layer different from the first layer;
   the first layer includes elevation structures that define a trench in the first layer, the trench having a bottom wall and two side walls;
   the material is positioned on the bottom wall and on the two side walls and on top of the elevation structures;
   the trench accommodates at least a part of the second electrode; and
   the second electrode does not substantially cover the material formed on top of the elevation structures.

2. The device of claim 1, wherein the material is formed in multiple spatially separated bands across the trench and the elevation structures.

3. The device of claim 1, wherein the material on top of the elevation structures has one or more grooves or holes.

4. The device of claim 1, wherein:
   the sensor is configured as a capacitive sensor;
   the physical parameter is humidity; and
   the material includes at least one of: a metal oxide, $SiO_2$, SiC, a polyester, Polymethyl methacrylate, Benzocyclobutene, a polysulfate, cellulose acetate butyrate, porous silicon, and silicon nitride.

5. The device of claim 1, comprising a transponder accommodating the sensor.

6. A device comprising a sensor for sensing a magnitude of a physical parameter of an environment of the sensor, wherein:
   the sensor comprises a first electrode, a second electrode and a material between the first and second electrodes;
   the material has an electrical property, whose value depends on the magnitude of the physical parameter;
   the first electrode is formed in a first layer, and the second electrode is formed in a second layer different from the first layer;
   the first layer has a trench and an elevation next to the trench;
   the trench has a bottom wall and a side wall;
   the material is positioned on the bottom wall and on the side wall and on top of the elevation;
   the trench accommodates at least a part of the second electrode; and
   the second electrode does not substantially cover the material formed on top of the elevation;
   wherein the material is formed in multiple spatially separated bands across the trench and the elevation.

7. The device of claim 6, wherein:
   the sensor is configured as a capacitive sensor;
   the physical parameter is humidity; and
   the material includes at least one of: a metal oxide, $SiO_2$, SiC, a polyester, Polymethyl methacrylate, Benzocyclobutene, a polysulfate, cellulose acetate butyrate, porous silicon, and silicon nitride.

8. The device of claim 6, comprising a transponder accommodating the sensor.

9. A device comprising a sensor for sensing a magnitude of a physical parameter of an environment of the sensor, wherein:

the sensor comprises a first electrode, a second electrode and a material between the first and second electrodes;

the material has an electrical property, whose value depends on the magnitude of the physical parameter;

the first electrode is formed in a first layer, and the second electrode is formed in a second layer different from the first layer;

the first layer has a trench and an elevation next to the trench;

the trench has a bottom wall and a side wall;

the material is positioned on the bottom wall and on the side wall and on top of the elevation;

the trench accommodates at least a part of the second electrode; and the second electrode does not substantially cover the material formed on top of the elevation;

wherein the material on top of the elevation has one or more grooves or holes.

10. The device of claim 9, wherein:

the sensor is configured as a capacitive sensor;

the physical parameter is humidity; and the material includes at least one of: a metal oxide, $SiO_2$, SiC, a polyester, Polymethyl methacrylate, Benzocyclobutene, a polysulfate, cellulose acetate butyrate, porous silicon, and silicon nitride.

11. The device of claim 9, comprising a transponder accommodating the sensor.

\* \* \* \* \*